United States Patent [19]
Clement

[11] Patent Number: 5,256,160
[45] Date of Patent: Oct. 26, 1993

[54] MEDICAL DEVICE VALVING MECHANISM

[75] Inventor: Thomas P. Clement, Bloomington, Ind.

[73] Assignee: Mectra Labs, Inc., Bloomfield, Ind.

[21] Appl. No.: 764,366

[22] Filed: Sep. 23, 1991

Related U.S. Application Data

[63] Continuation-in-part of Ser. No. 660,356, Feb. 22, 1991, Pat. No. 5,203,769, which is a continuation-in-part of Ser. No. 432,084, Nov. 6, 1989, Pat. No. 5,019,054.

[51] Int. Cl.$^5$ .................. A61M 37/00; B65D 1/24
[52] U.S. Cl. ............................. 604/319; 220/502; 220/525
[58] Field of Search ................... 604/317–319, 604/321, 322, 324, 326; 220/502, 525, 528

[56] References Cited

U.S. PATENT DOCUMENTS

| | | |
|---|---|---|
| 628,907 | 7/1899 | Hart . |
| 786,215 | 3/1905 | Hepnar . |
| 811,111 | 1/1906 | Wegefarth . |
| 1,658,754 | 2/1928 | Wood . |
| 2,355,620 | 8/1944 | Bower, Jr. et al. ............ 604/317 |
| 2,636,646 | 4/1953 | Olsen .......................... 220/502 |
| 3,012,752 | 12/1961 | Buck . |
| 3,048,192 | 8/1962 | Murphy, Jr. . |
| 3,081,770 | 3/1963 | Hunter . |
| 3,157,201 | 11/1964 | Littmann . |
| 3,434,691 | 3/1969 | Hamilton . |
| 3,467,082 | 9/1969 | Gilbert . |
| 3,783,900 | 1/1974 | Waldbillig . |
| 3,788,602 | 1/1974 | Kitzie . |
| 3,794,032 | 2/1974 | Derouineau . |
| 3,833,000 | 9/1974 | Bridgman . |
| 3,834,372 | 9/1974 | Turney . |
| 3,843,016 | 10/1974 | Bornhorst et al. ............ 604/319 |
| 3,957,082 | 5/1976 | Fuson et al. . |
| 4,079,737 | 3/1978 | Miller . |
| 4,173,328 | 11/1979 | Karbo . |
| 4,230,128 | 10/1980 | Aramayo . |
| 4,261,468 | 4/1981 | Krebs ........................ 220/525 |
| 4,280,498 | 7/1981 | Jensen . |
| 4,282,873 | 8/1981 | Roth . |
| 4,299,217 | 11/1981 | Sagae et al. . |
| 4,314,586 | 2/1982 | Folkman . |
| 4,397,335 | 8/1983 | Doblar et al. . |
| 4,443,220 | 4/1984 | Hauer et al. . |
| 4,540,156 | 9/1985 | Cross . |
| 4,553,964 | 11/1985 | Sasaki . |
| 4,566,480 | 1/1986 | Parham . |
| 4,568,332 | 2/1986 | Shippert . |
| 4,581,014 | 4/1986 | Millerd et al. . |
| 4,593,717 | 6/1986 | Levasseur . |
| 4,595,005 | 6/1986 | Jinotti . |
| 4,605,396 | 8/1986 | Tseo et al. . |
| 4,642,097 | 2/1987 | Siposs . |
| 4,643,197 | 2/1987 | Greene et al. . |
| 4,645,496 | 2/1987 | Oscarsson . |
| 4,648,868 | 3/1987 | Hardwick et al. . |
| 4,654,027 | 3/1987 | Dragan et al. . |

(List continued on next page.)

FOREIGN PATENT DOCUMENTS

| | | |
|---|---|---|
| 3528656 | 7/1986 | Fed. Rep. of Germany . |
| 991478 | 5/1965 | United Kingdom . |

*Primary Examiner*—Ralph Lewis
*Attorney, Agent, or Firm*—Barnes & Thornburg

[57] ABSTRACT

A disposable sample trap system having a cylindrical hollow sample trap body formed with a bottom end wall and an upper open end and with multiple dividers extending across the hollow of the body to divide the hollow of the body into a plurality of chambers, a cap rotatably attached to and sealing said open end of the trap body, and inlet and outlet conduit attached to an opening in the cap to allow for passage of fluid and samples through the cap opening into one of the plurality of chambers which is aligned with the opening and subsequently out of the trap, wherein there are narrow slots in the dividers to fluidly connect the inlet conduit to the outlet conduit through the plurality of chambers so that when the outlet conduit is connected to a vacuum source, the vacuum causes fluid and samples to be drawn into the one of the plurality of chambers through the inlet passage while allowing the fluid entering into the one of the plurality of chambers to pass through at least one of the narrow slots to the outlet and trapping the sample in the one of the plurality of chambers, since the sample cannot pass through the slot.

4 Claims, 9 Drawing Sheets

U.S. PATENT DOCUMENTS

| | | |
|---|---|---|
| 4,667,927 | 5/1987 | Oscarsson . |
| 4,758,235 | 7/1988 | Tu . |
| 4,807,666 | 2/1989 | Morse . |
| 4,809,860 | 3/1989 | Allen .................................. 604/319 |
| 4,846,800 | 7/1989 | Ouriel et al. ........................ 604/319 |
| 4,880,411 | 11/1989 | Fangrow, Jr. et al. ............. 604/319 |
| 4,911,202 | 3/1990 | Nelson . |
| 4,925,450 | 5/1990 | Imonti et al. . |
| 4,966,551 | 10/1990 | Betush . |

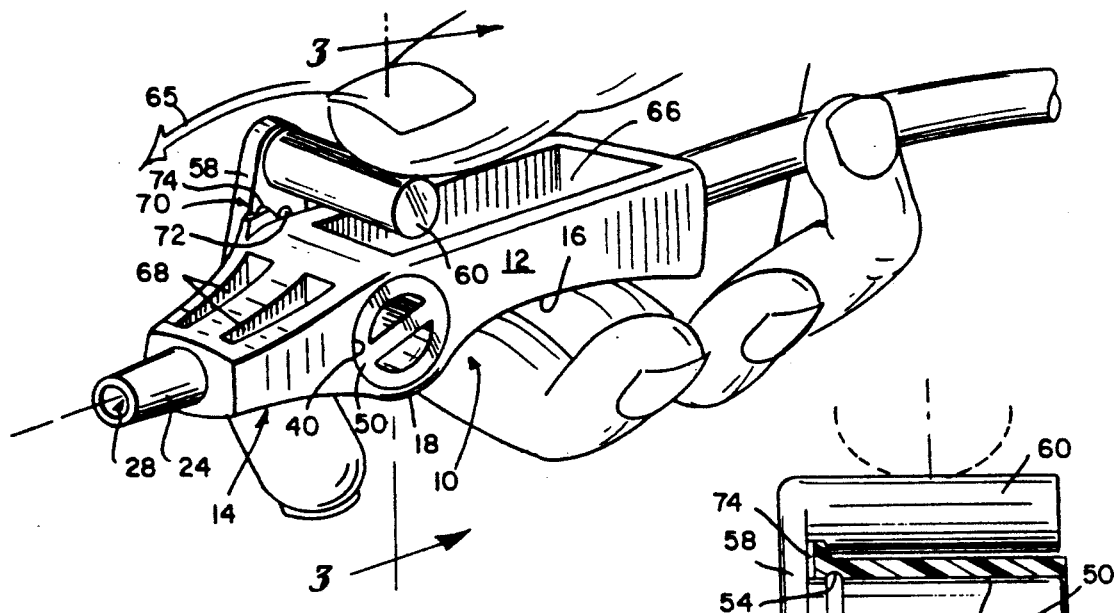
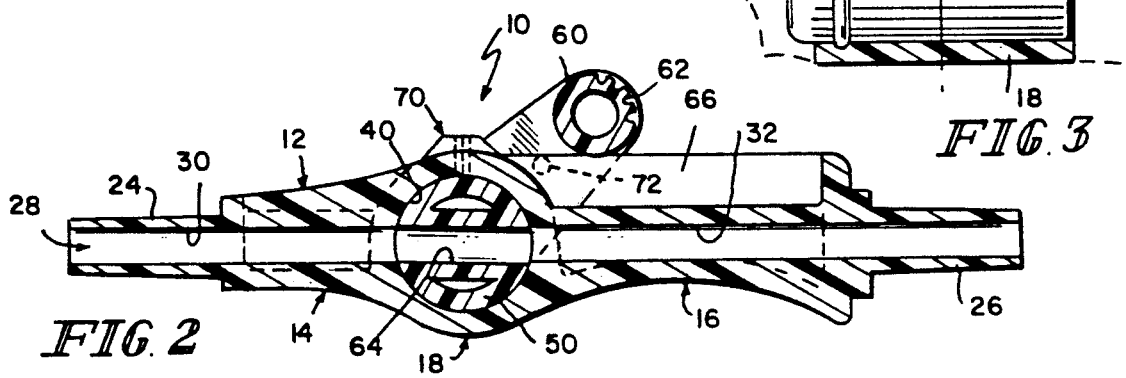
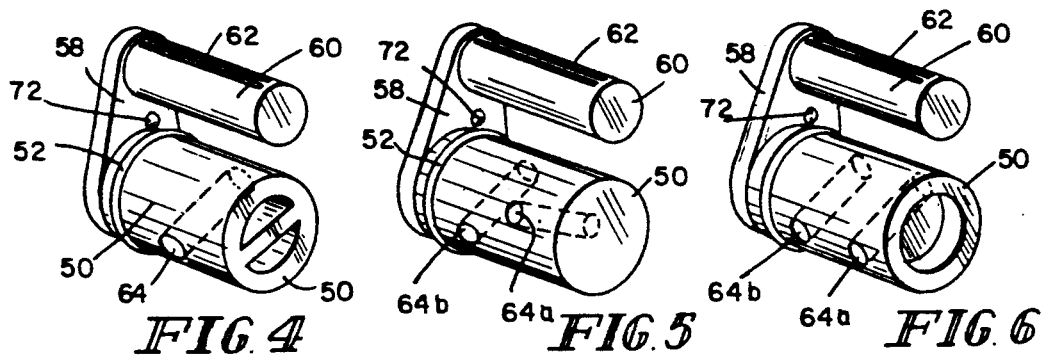
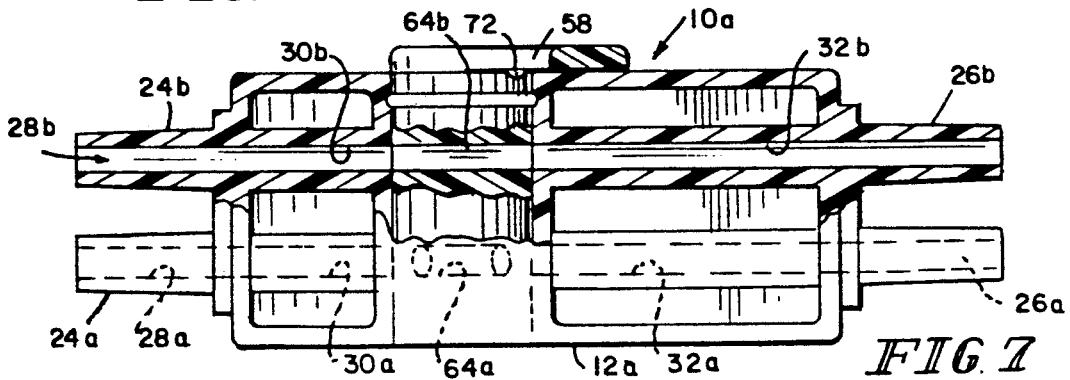

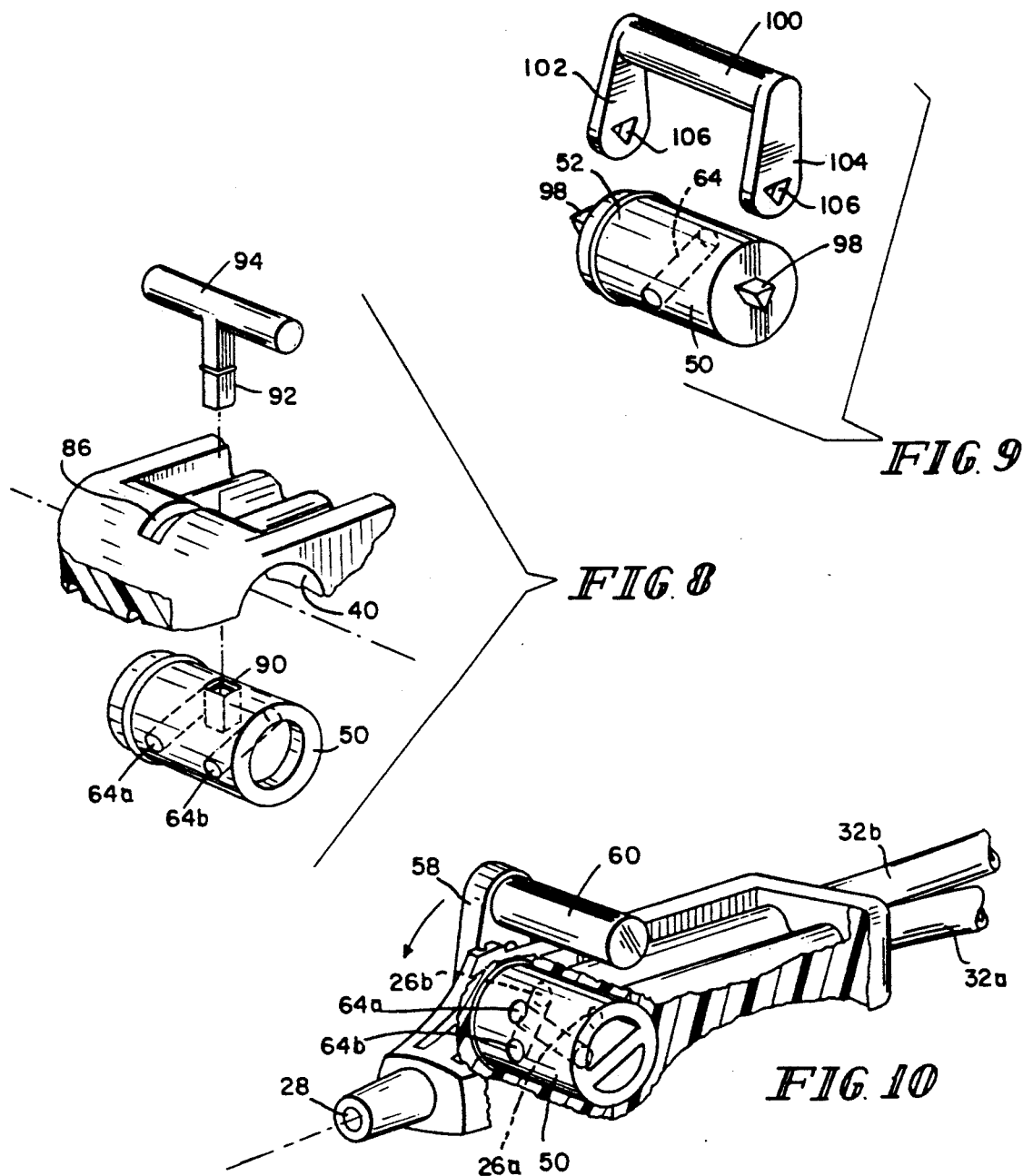

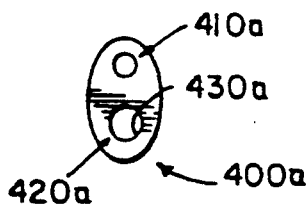 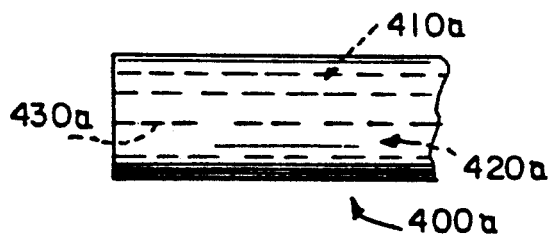
FIG. 16  FIG. 17
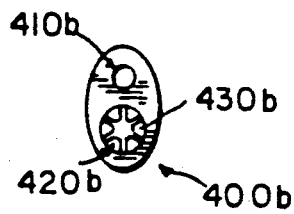 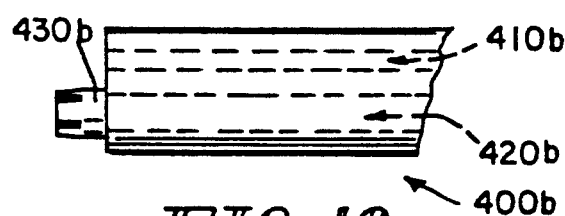
FIG. 18  FIG. 19
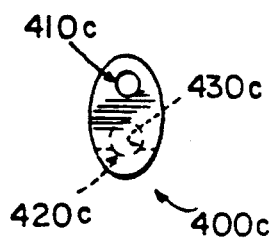 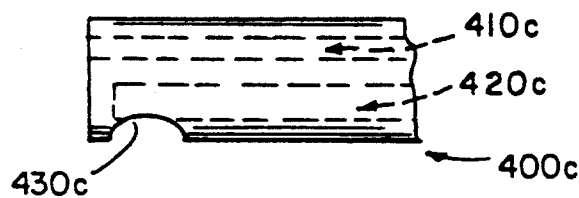
FIG. 20  FIG. 21
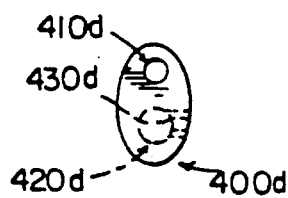 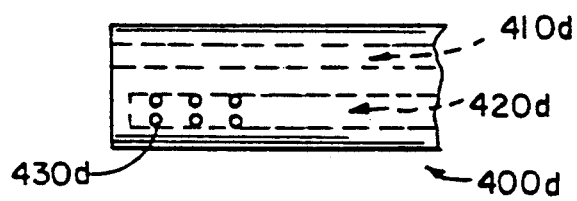
FIG. 22  FIG. 23
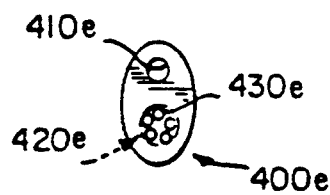 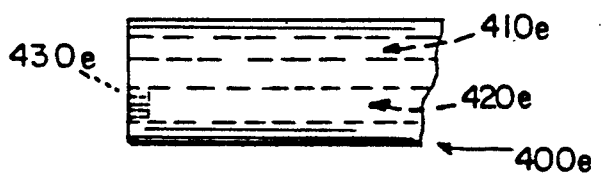
FIG. 24  FIG. 25
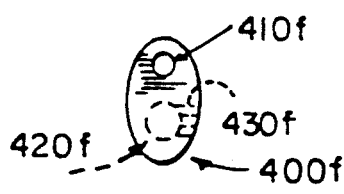 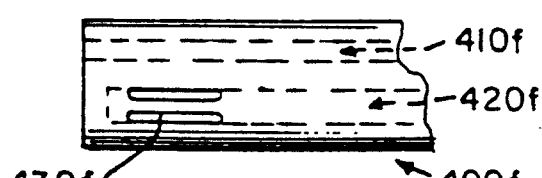
FIG. 26  FIG. 27

MEDICAL DEVICE VALVING MECHANISM

This is a continuation-in-part application of co-pending U.S. application "Medical Device Valving Mechanism", U.S. application Ser. No. 07/660,356, filed Feb. 22, 1991, now U.S. Pat. No. 5,203,769 which is a continuation-in-part application of U.S. application Ser. No. 07/432,084, which issued May 28, 1991 as U.S. Pat. No. 5,019,054 to Clement et al.

FIELD OF THE INVENTION

The present invention relates to medical devices employed for trapping samples of body tissue or fluids, and more particularly to the provision of a combination sample trap and a valve mechanism. In preferred embodiments the valve mechanism may be held securely in one hand and operated by the thumb of that hand to open and close a valve passageway leading into the sample trap.

BACKGROUND OF THE INVENTION

In recent years, medical procedures have been developed which involve the connection of fluid tubes between the patient and various instruments including sources of fluid pumped into the patient and suction lines to remove fluid from the patient. All of this development activity has produced a need for a valving mechanism and delivery conduit which can be securely held and controlled by one hand, leaving the other hand free to perform other functions. Since these mechanisms necessarily must be low-cost disposable mechanisms, the conventional prior art designs will not satisfy the requirements for several reasons. The prior art devices are usually too complex and costly to be thrown away when they are contaminated with body fluids. Also, the prior art devices are typically unwieldly and difficult to hold and control with one hand. An example of a prior art medical valve is shown in U.S. Pat. No. 4,568,332 issued to Ronald D. Shippert Feb. 4, 1986. The Shippert valve, which is designed for use in suction lipectomy, is made from metal and is fabricated from a multitude of parts which must be assembled together in a complex assembly system.

BRIEF DESCRIPTION OF THE INVENTION

The medical device valving mechanism of the present invention comprises an elongated valve body molded to have a longitudinal extending body shaped to be gripped and securely held in a user's hand leaving the hand's thumb free for valve operational movement. The valve body provides at least one passageway extending longitudinal therethrough, and also provides a cylindrical opening or rotor bore extending transversely therethrough and intercepting the at least one passageway. A cylindrical molded plastic, one-piece rotor is provided for snug, slidable and rotational insertion into the cylindrical opening to block the said at least one passageway, the rotor being rotatable about its axis between valve opening and valve closing positions. The rotor has at least one transaxially extending passageway therethrough which opens the at least one fluid passageway through the valve body when the rotor is in its valve opening position and which closes the at least one fluid passageway when the rotor is in its valve closing position. The valving mechanism also comprises thumb-actuated means connected to the rotor for rotating the rotor between its positions, the actuating means being disposed above the valve body and the rotor for convenient thumb movement of the rotor. Connected to the valve body in fluid communication with at least one fluid passageway is a conduit piece that channels and directs the flow of fluid leaving or entering the valve body. The conduit piece can be curved with respect to the valve body to extend either upward, downward, or sideways. In certain embodiments the conduit piece can be divided into two or more fluid conduit portions for use with dual valves, and can also extend along a complex curve to direct fluid flow both downward and sideways with respect to the valve body. The conduit piece can be attached to the valve body as an integrally molded piece or separately formed as a snap-on piece that connects in fluid tight communication with the valve body.

The valve body of the present invention is preferably molded to have a forward bottom portion shaped to be gripped by the index finger of one hand and a rearward bottom portion shaped to be gripped by the middle finger of the hand with a depending transverse bottom portion between the forward and rearward portions. The middle transverse bottom portion is preferably directly below the cylindrical opening which holds the rotor to be disposed partially between the index and middle finger for stabilization. Further, the rearward bottom portion is preferably transversely recessed to provide a comfortable gripping surface.

In preferred embodiments, the valve can be utilized as a component of a sample trap system. For example, a surgeon could direct the integrally attached conduit piece in fluid communication with a vacuum source to remove body tissue and fluid from a patient. Since laboratory analysis of such tissue or fluid samples is often required, an apparatus or method for trapping or otherwise holding the sample for later recovery is needed. Using a valve of the present invention, a low cost, disposable sample trap can be constructed.

In one embodiment of a sample trap, a valve body shaped to be gripped and securely held while leaving a thumb free for valve operational movement is provided. The valve body provides first and second passageways alternately in fluid communication with a third passageway, and also is formed to define a cylindrical opening extending transversely therethrough and in fluid communication with the passageways. A cylindrical rotor is snug slidably and rotationally inserted into the cylindrical opening. The rotor has two transaxial passageways therethrough to provide alternate fluid communication between the first passageway and the third passageway, and the second passageway and the third passageway. A thumb-actuated arm for rotating said rotor is also provided. The system also includes an airtight container formed to define a chamber for holding tissue or liquid samples. An inflow conduit for connecting one of the first or second passageways of the valve body to the container in airtight fluid communication, and outflow conduit for connecting the container in fluid communication to a vacuum source are also connected to the airtight sample container.

Preferably, the first passageway is connected to the vacuum source and the second passageway is connected to the inflow conduit. To prevent passage of solid tissue samples from the container through the outflow conduit, a filter screen is positioned in the chamber of the container. The filter screen is in fluid communication with the outflow conduit and has a plurality of apertures therethrough to allow passage of air and reduce admittance of tissue into the outflow conduit. An in-line filter can also be positioned in the outflow conduit to reduce passage of tissue through the outflow conduit.

In yet another alternative embodiment of the invention, a disposable sample trap system includes a sample trap body formed to define a plurality of chambers, with each chamber being configured to have an entrance and an exit. Filter elements may be positioned to inhibit passage of sample out of the exit of each chamber. Tissue or fluid samples are admitted through a cap into the chambers of the sample trap body and air pressure within the sample trap body is controlled to alternately pull together in sealing engagement the cap and the sample trap body, or allow release and disengagement of the cap and sample trap body.

In a preferred embodiment, the sample trap body may be cylindrically configured, and each chamber defined in the sample trap body may also be cylindrically configured. It will be appreciated, however, that the individual chambers may take several forms with the chambers radially spaced apart about the axis. The chambers may be symmetrically arranged and positioned at substantially identical radial distances from the center of the cylindrical sample trap body. In those configurations in which the sample trap body is cylindrically configured, the cap may also be cylindrically configured and dimensioned to fit over the sample trap body. A sample conduit, defined to extend through the cap, is positioned from the center of the cap at a radial distance substantially identical to the radial distance of the chambers from the center of the sample trap body so that each chamber is brought into fluid communication with the sample conduit as the cap is rotated relative to the sample trap body.

The sample trap body may be formed to define external threads and the cap may be formed to define internal threads threadingly engagable with the external threads. The external and internal threads may be arranged to prevent inadvertent disengagement of the cap from the sample trap body. In addition, the sample trap body may be formed to define an exit chamber in fluid communication with the exits of each chamber. This exit chamber may be connected in fluid connection with a valve such as previously described to control admission of air into the exit chamber, or bring the exit chamber into fluid communication with a vacuum source to reduce air pressure in the sample trap body.

In alternative embodiments, a vacuum controlled disposable sample trap system for holding samples is provided. The trap system includes a sample trap body formed to define a plurality of chambers and a cap formed to define a sample conduit for admitting samples drawn by a vacuum into the chambers of the sample trap body. The cap is movable with respect to the sample trap body to allow positioning of the sample conduit in communication with each chamber. The cap is attached to the sample trap body.

In some embodiments, the sample trap system includes a mechanism for reducing air pressure in the chambers of the sample trap body. Reducing air pressure acts to draw samples from the sample conduit into each one of the chambers as the cap is moved to position the sample conduit in communication with each chamber. This air pressure reducing mechanism may include a vacuum conduit defined in the cap.

Additionally, the sample trap body may be formed with dividers defining the plurality of chambers. The chambers are open at their upper ends, and apertures defined in the dividers provide gas communication between the chambers to permit evacuation of air from all chambers. The sample trap body may be cylindrically formed to have an open upper end closed by the cap, with the cap being rotatably movable about the sample trap body.

In other embodiments, a disposable sample trap for medical use to draw tissue and other samples from a body includes sample trap container means for containing a sample. The container means is divided into a plurality of chambers into which samples are deposited. A vacuum conduit for evacuating air from the plurality of chambers, and a sample conduit for communicating with the plurality of chambers are also provided. The sample conduit can be moved selectively into communication with each of the plurality of chambers to deposit and retain samples in each of the plurality of chambers. It is contemplated that the vacuum conduit and the sample conduit may be positioned in communication with either different chambers or the same chambers.

It is an object of this invention to provide a sample trap system employing a disposable rotary valve connected to a sample holding container.

It is another object of this invention to provide a low-cost, disposable rotary sample trap that can be connected to a disposable rotary valve.

It is yet another object of this invention to provide a sample trap container divided into a plurality of chambers that can be moved into communication with a sample conduit and a vacuum conduit, the vacuum conduit being connectable to a vacuum source and the sample conduit being connectable to medical devices utilized to retrieve bodily tissues, fluids, or other medical samples.

Other objects and features of the present invention will become apparent as this description progresses.

BRIEF DESCRIPTION OF THE DRAWINGS

FIG. 1 is a perspective view of the valving mechanism of the present invention showing the mechanism held by one hand with the thumb of the hand controlling the valve rotor;

FIG. 2 is a longitudinal sectional view of the mechanism of FIG. 1;

FIG. 3 is a sectional view taken along the lines 3—3 in FIG. 1;

FIGS. 4, 5 and 6 are perspective views of various rotor bodies for the mechanism of FIG. 1;

FIG. 7 is a longitudinal sectional view of a different embodiment showing two separate passageways through the valve, both controlled by a valve rotor;

FIG. 8 shows an alternative rotor control means;

FIG. 9 shows another alternative rotor control means;

FIG. 10 shows yet another embodiment;

FIGS. 16-27 illustrate alternative distal ends of conduit pieces;

FIGS. 28-30 illustrate a flexible conduit piece, with FIGS. 29 and 30 respectively being views along lines 29a-29a and 30a-30a;

DETAILED DESCRIPTION OF THE DRAWINGS

Figure 11:
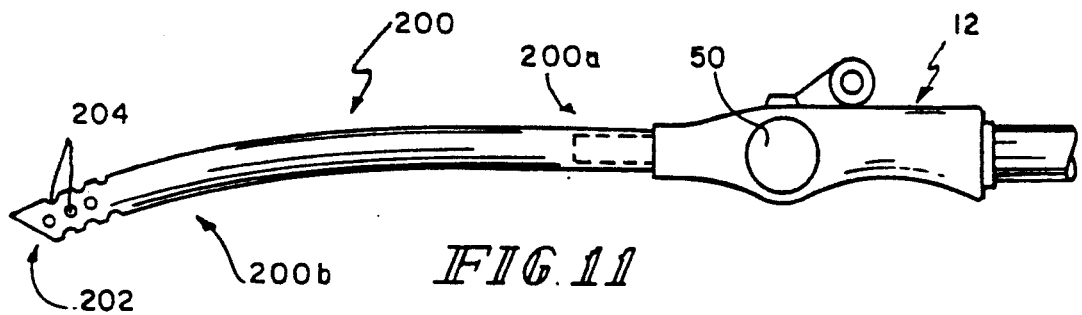
FIG. 11 shows a valve body fitted with a snap-on, friction tight conduit piece that directs fluid leaving the valve body to a conduit piece tip formed to have a plurality of apertures.

A valving mechanism 10 in accordance with the present invention is shown in perspective view held by a right-hand in FIG. 1. In the drawings, and in this description, like reference numerals represent like parts. The illustrative mechanism 10 is shown comprising a valve body 12 which is illustrated as being a molded plastic, one-piece, elongated valve body molded to have a longitudinally extending body shaped to be gripped and securely held in either hand leaving the hand's thumb free for valve operational movement.

The illustrative valve body 12 is formed at its bottom surface to provide a forward bottom portion 14 shaped to be gripped by the index finger of one hand and a rearward bottom portion 16 shaped to be gripped by the middle finger and, depending upon the size of the hand, by the fourth finger of the hand, with a depending transverse bottom portion 18 between the forward and rearward portions 14, 16. It will be appreciated from the sectional view of FIG. 2 that the recessed portions 14, 16 are smoothly transversely recessed for gripping comfort while the depending central portion 18 is smoothly rounded to fit between the index and middle fingers. It will further be appreciated that, in this description and in the appended claims, statements such as "engaged by the index finger" and "engaged by the middle finger" are intended to indicate the general shape and size of an adult's hand relative to the mechanism 10 and that the body 12 is proportioned and shaped to be held generally by the index and middle fingers pressing the body against the palm of the hand, leaving the thumb free for movement to control the mechanism.

The valve body 12 is further provided with a forward nipple 24 and rearward nipple 26 to which vacuum lines or fluid lines of different types may be connected. These nipples 24, 26 are longitudinally aligned with a passageway 28 formed to extend longitudinally through the valve body 12 when the valve body is molded. The illustrative passageway 28, best seen in FIG. 2, includes a forward passageway portion 30 and a rearward passageway portion 32. In this description and in the appended claims, the term "at least one fluid passageway" is intended to define one or more passageways extending longitudinally through the valve body 12. It will be appreciated, as this description progresses, that the valve body may have, for instance, one, two or even three or more such passageways extending longitudinally therethrough and lying generally in the same plane such that their axes will generally intersect the axis of the valve rotor to be discussed hereinafter. It will further be appreciated that a valve body 12 may be formed to have, for instance, one forward passageway portion 30 and two parallel rearward passageways 32 which may be connected by the valve rotor to be described hereinafter. In summary, concerning the number of passageways, within the scope of the present invention, the valving mechanism 10 may be provided with one or more passageways therethrough and the passageways may be connected in different combinations by the movement of the rotor.

The valve body 12 is molded to provide a cylindrical opening or bore 40 extending transversely through the valve body and illustratively, just above the central body portion 18 which is held between the index and middle fingers of the hand. This cylindrical opening 40 is positioned to intercept the passageway 28 through the valve body as best seen in FIG. 2. A cylindrical, molded plastic, one-piece rotor 50 is snugly and slidably rotatably inserted in the opening 40 to block the passageway 28 except when the rotor is in its passageway opening position.

The body 12 may preferably be molded from a fairly rigid material such as a polycarbonate plastic while the core 50 may preferably be molded from a softer plastic such as a polypropylene, nylon or teflon. The closeness of the snug fit of the rotor 50 in the bore 40 and the nature of the material from which the body 12 and rotor 50 are molded will determine the pressure capacity of the valving mechanism. It will be appreciated that a very snug rotor 50 fit in the bore 40 will accommodate high pressure. The rotor is provided with a peripherally extending ridge 52 integrally molded thereon to be snapped into a groove 54 formed in the bore 40 for the rotor.

Thus, when the softer plastic rotor 50 is inserted into the cylindrical opening or bore 40 so that the ridge 52 engages the groove 54, the valve rotor assembly will be fixed in the valve body 12 to complete the valving mechanism of the illustrative embodiment of FIG. 1. This very simple and easy assembly process is extremely attractive from an assembly cost point of view and from an operational point of view. In the illustrative embodiments of FIGS. 1-6, the rotor 50 is integrally molded and formed to have a one-piece thumb-actuated means for rotating the rotor. That is, as best illustrated in the drawings, the rotor 50 is molded to have a radially upwardly extending connecting portion 58 and a thumb engaging portion 60 extending generally parallel to and above the rotor 50. This engaging portion 60 may be serrated as indicated at 62 to provide a gripping surface for the thumb.

In FIGS. 1-4, the illustrative rotor 50 is provided with a single transaxially extending passageway 64 which is shown in alignment with the passageway portions 30, 32 in FIG. 2. When the rotor is rotated, however, the passageway 28 and its portions 30, 32 will be blocked by the rotor 50. Thus, the rotor 50 rotates between its valve opening position shown in FIG. 2 and a valve closing position 45° removed from that shown in FIG. 2. It will be appreciated that the valve rotor 50 may be moved to its closing position simply by pushing forwardly on the thumb engaging portion 60 as suggested by the arrow 65 in FIG. 1. The valve body 12 may be molded in a conventional fashion to have cavities such as illustrated at 66 and 68 to use less plastic material and to make the valve body lighter and easier to hold. It will also be appreciated that the valve body 12 may be formed with detent means indicated at 70 which will give the medical personnel a feeling for when the rotor 50 is in its desired position. A detent means 70 may include, for instance, a protrusion 72 on the connecting portion 58 of the rotor which must move past a resilient protrusion 74 on the valve body.

Referring further to FIGS. 4, 5 and 6, it will be seen that, while FIG. 4 shows a single passageway 64 in the valve rotor 50, FIG. 5 shows transversely spaced apart passageways 64a and 64b which are 90° spaced apart. It will further be seen that FIG. 6 shows two transversely spaced apart passageways 64a and 64b formed in the rotor 50 to accommodate two parallel passageways through the valve body 12. It will be appreciated that, within the scope of this invention, there may be a wide variety of combinations of passageways 64a, 64b with the passageways arranged to open and close the passageways 28a, 28b at various rotor 50 positions. The passageways 28a, 28b may be opened and closed together or alternately opened and closed. The valve positions of the rotor 50 may be selected to be 45° apart or 90° apart or any selected angle sufficient to provide full closing and opening.

Referring then to FIG. 7, it will be seen that there is illustrated a valving mechanism 10a having a valve body 12a formed to include parallel, side by side, longitudinally extending passageways 28a and 28b. These passageways 28a, 28b are formed to have the forward portions 30a, 30b and rearward portions 32a, 32b connecting, respectively, the forward nipples 24a, 24b and the rearward nipples 26a, 26b. When a rotor such as that illustrated in FIG. 5 is inserted into the valve body 12a of FIG. 7, the passageway 28a is open when the passageway 28b is closed and vice versa. When the rotor assembly of FIG. 6, however, is inserted into the valve body 12a, both passageways 28a, 28b are opened and closed by the same movement of the rotor 50.

In FIG. 8, there is illustrated a valve body having an elongated slot 86 just above the rotor 50, and the rotor 50 is illustrated as having an opening 90 therein for receiving a stem 92 which extends downwardly through the slot 86 to provide a driving connection for the rotor 50. The upper end of this stem 92 carries a crossbar 94 or thumb engaging portion. In the embodiment of FIG. 8, for instance, the stem 92 may be designed to snap into the opening 90 to make a permanent connection between the stem and the rotor 50.

Referring to FIG. 9, it will be seen that another approach for providing a driving connection between the operator's thumb and the rotor 50 is illustrated. In the FIG. 9 structure, the axially outer ends of the rotor 50 are provided with first engaging means 98. A saddle bar 100 is provided for thumb engagement, the saddle bar having depending sides 102, 104 which are formed to provide second engaging means 106 at the lower ends. Illustratively, the first engaging means 98 are male connectors which snap inwardly into the triangularly shaped female connectors of engaging means 106.

Referring to FIG. 10, still another embodiment is shown. In the FIG. 10 embodiment, the valve body has two input passageways 32a, 32b, but only one output passageway 28. (Again, like reference numbers represent like parts.) The rotor 50 in the FIG. 10 embodiment is designed to connect the passageways 26a, 26b alternatively to the passageway 28. Specifically, the passageways 64a, 64b in the rotor 50 connect the passageways 26a, 26b to the passageway 28 depending upon the position of the rotor.

FIG. 11 illustrates an embodiment of the invention in which the valve body 12 is fitted with a conduit piece 200 that extends away from the valve body 12 in the valve body 12's direction of elongation before slightly curving downward with respect to the valve body 12. The conduit piece 200 is attached at its proximal end 200a to the valve body 12 and projects outward for interaction with a patients body at its distal end 200b. The amount of fluid introduced into or withdrawn through the conduit piece 200 is controlled by rotation of the rotor 50. Fluid can travel through the conduit piece 200 either toward or away from the valve body 12, respectively depending on whether aspiration or lavage is required. Fluid passing away from the valve body 12 can exit the conduit piece 200 at the terminal outlet 202 and through a plurality of apertures 204 defined in the conduit piece 200.

Figure 12:
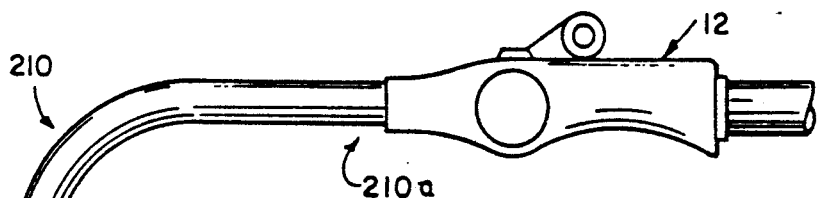
FIG. 12 show the valve body of FIG. 11 fitted with a sharply curving tip useful in dental procedures.

FIG. 12 illustrates the valve body 12 of FIG. 11 connected to a conduit piece 210. The conduit piece 210 sharply curves downward and back toward the valve body 12 so that fluid entering the conduit piece 210 is constrained to reverse its direction of flow before exiting the conduit piece 210 at outlet 212. This is of particular advantage for dental procedures in which portions of the mouth not readily reached by linearly extending or slightly curving conduit pieces such as shown in FIG. 11.

Figure 13:
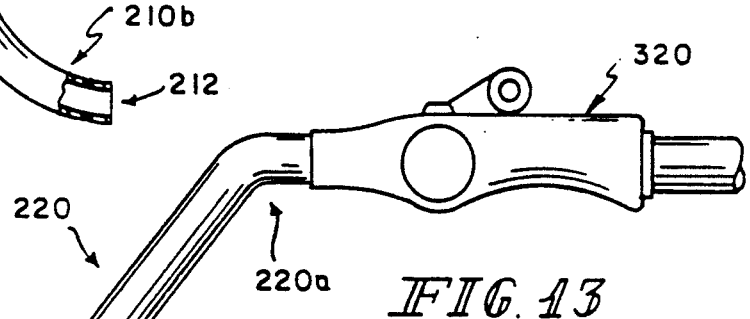
FIG. 13 shows an integrally molded conduit piece and valve body, with the conduit piece being bent to provide a sharply downturning channel for fluid flow relative to the valve body.

FIG. 13 illustrates a sharply downturning conduit piece 220 integrally formed from molded plastic with a valve body 320. Fluid directed through the valve body 320 is directed through the conduit 220 and exits at outlet 222.

Figure 14:
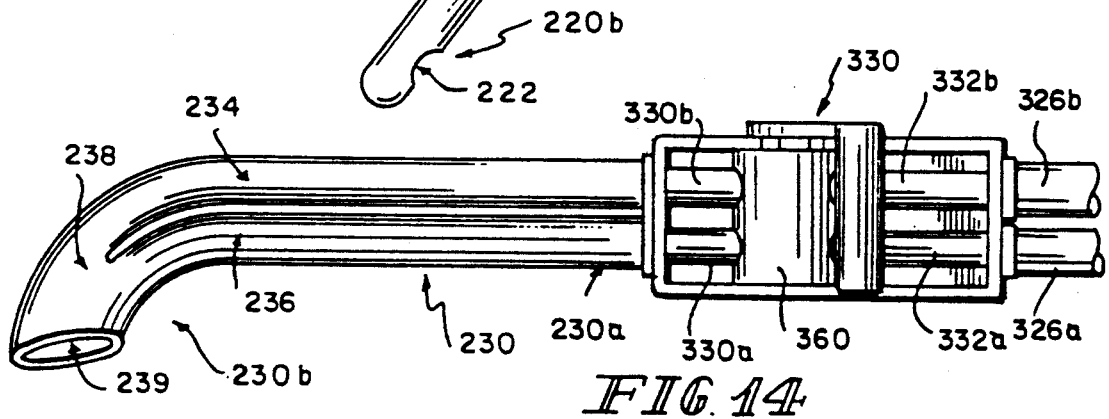
FIGS. 14 and 15 are respectively top and side views of a dual valve having two fluid conduits controlled by a rotor valve, both conduit pieces being configured to curve sideways and downward with respect to the valve body.
Figure 15:
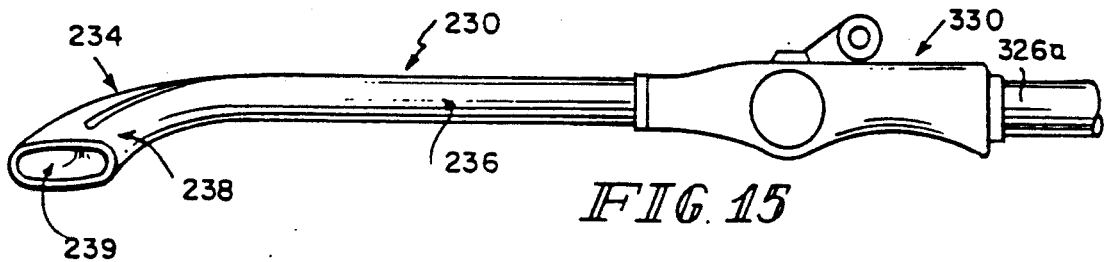

FIGS. 14 and 15 respectively illustrates top and side views of a dual valve 330 connected to a dual conduit piece 230. The dual valve 330 is similar to that shown in FIG. 7 and has a fluid inlet 326b and a vacuum port 326a. Fluid introduced into passageway 332b travels through a passageway (not shown) in the rotor 360 and into a passageway 330b. Fluid leaving the passageway 330b is directed along a curving first conduit piece 234 until it meets with a second conduit piece 236 at a common conduit 238. The fluid can then exit the common conduit 238 at its port 239.

Fluid can be drawn into the common conduit 238 through the port 239 by connection of the valve body 330 to a vacuum source (not shown). In the embodiment shown, the vacuum source is connected to the vacuum port 326a, and in controlled fluid communication with the common conduit 238 by way of passageways 332a, 330a and conduit piece 236. Application of the vacuum is controlled by the position of the rotor 360 separating the passageways 332a and 330a. The interconnecting passageways (not shown) in the rotor are configured as shown in FIG. 7 so that neither the passageways 330b, 332b or 330a, 332a are simultaneously in fluid communication with each other. This arrangement permits an operator to control both fluid delivery and aspiration with one handed operation.

As illustrated in FIGS. 16-27, the distal end of a conduit piece can include a wide variety of configurations (For example, conduit piece tips 400a through 400f) that are suitable for use in conjunction with single or dual port valves such as respectively shown in FIGS. 10 and FIGS. 14-15. Fluid can be delivered to patients through conduits 410a-410f and withdrawn by aspiration through conduits 420a-420f. Conduits 420a-420f can terminate with a simple opening 430a (conduit 420a); with multiple slots 430b (conduit 400b); with downwardly directed openings 420c (conduit 400c); with multiple sideways directed perforations 430d (conduit 400d); with multiple forward facing perforations 430e (conduit 400e); and with sideways directed slots 430f (conduit 400f).

Figure 28:
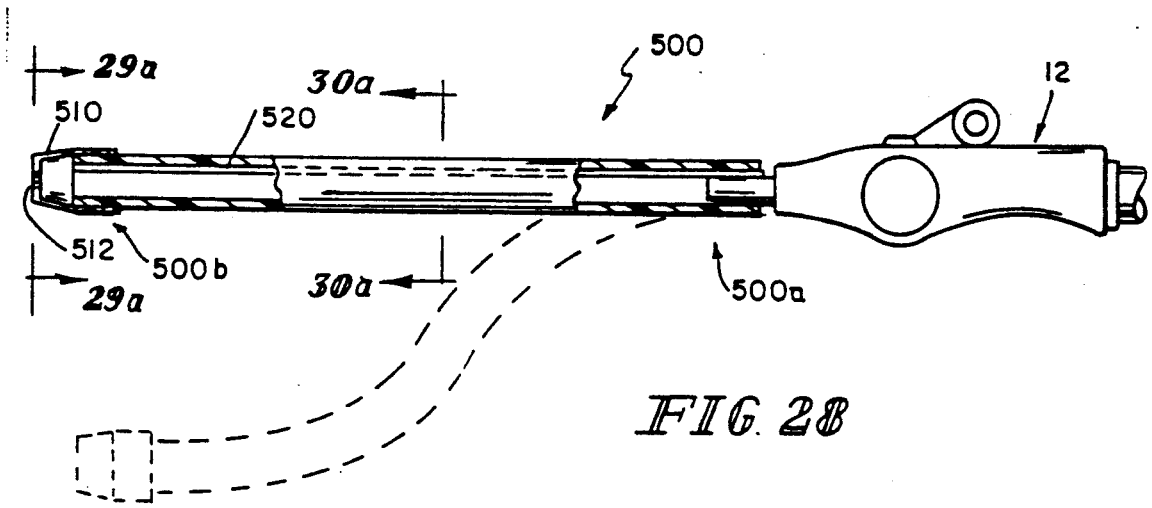
Figure 29:
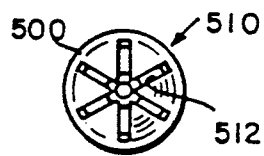
Figure 30:
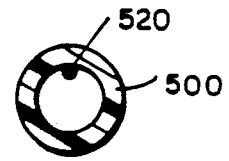

As illustrated in FIGS. 28, 29, and 30, the conduit piece does not have to be formed from a rigid piece snapped-on or integrally molded with the valve body 12. A flexible, resilient polymeric material such as rubber or polyethylene tubing can be formed into a conduit piece 500 (the conduit piece 500 terminates in a tip 510 having forward facing slots 512 to direct fluid flow). As outlined in dotted lines in FIG. 28, the conduit piece 500 can be easily redirected from a first position (in bold lines) so that its distal end 500b is positioned in a predetermined location without requiring movement of its proximal end 500a or attached valve body 12. A semi-rigid support element such as wire 520 can also be coupled to the conduit piece 500 to stabilize the shape of the conduit piece 500, holding it in any desired shape.

The present invention, therefore, provides a disposable, plastic stopcock handle-valve or lavage valving mechanism which a user can hold and operate with either hand. The body of the handle-valve has a contoured bottom surface that fits into enough of the palm side of either hand of the operator, starting with the index finger, to permit the operator to both operate the handle-valve and direct its motion. Importantly, for control purposes, the thumb engages an actuating means which is preferably disposed axially and longitudinally just above the rotor of the valve, and this actuating or engaging portion may be integrally molded with the rotor. For control purposes, the connecting portion 58 of the rotor assembly may have a moment-arm of approximately one inch and a stroke of approximately three-fourths inch, a comfortable span for either an adult female or male hand. The top extension of the thumb engaging portion may be serrated to facilitate its movement by the thumb and the bottom or other surfaces of the valve body may be serrated at convenient locations to provide a convenient and comfortable grip. The valve body 12 and the core 50 are assembled with a slight interference fit to provide a good seal between the body and the core without requiring extreme pressure in excess of that which is comfortable for an adult female or male to move by thumb action. A conduit piece is attached to the valve body in fluid communication said fluid passageway extending longitudinally through the valve body. This conduit piece has a proximal end attached to the valve body and a distal end projecting outward from the valve body for patient contact, and introduction of fluid into the conduit piece is controlled by rotation of the rotor with the thumb actuated controls.

Figure 31:
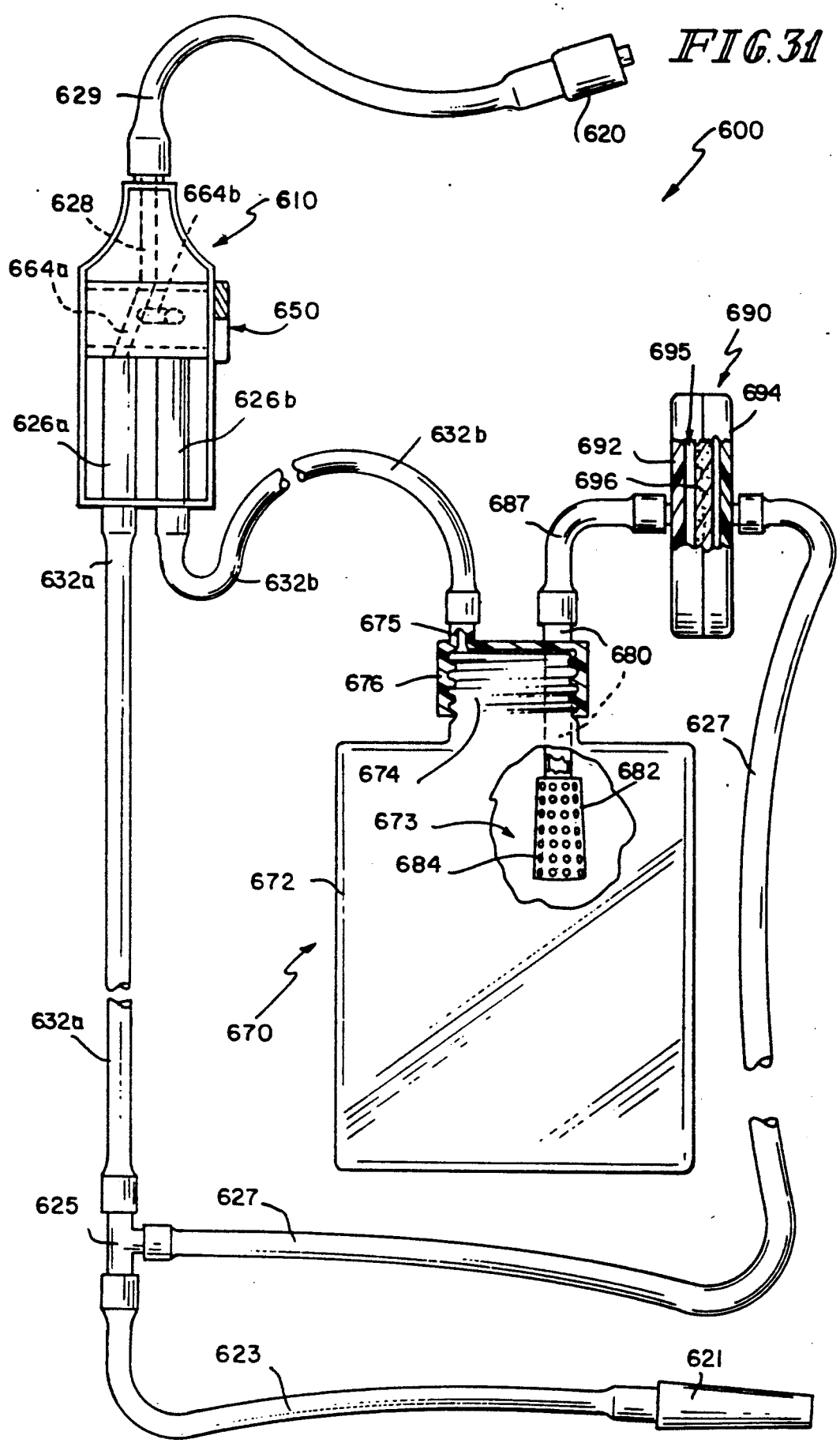
FIG. 31 is a view of a sample trap system employing the dual valve shown in FIG. 110. The dual valve is shown in a plan top view with the thumb rotated actuator partially cut away.

As shown in FIG. 31, a dual valve 610, similar to that previously described with reference to FIG. 10, can form a component of a sample trap system 600. The system 600 includes a valve 610 connected to container 670 for holding samples (not shown). The valve 610 is formed to define first and second passageways 626a and 626b. The passageways 626a and 626b are alternately operably connected in fluid communication with a third passageway 628 defined in the valve 610. A rotor 650, formed to define two transaxial passageways 664a and 664b, can be rotated between a first position in which passageway 664a connects in fluid communication third passageway 628 and first passageway 626a, and a second position (not illustrated) in which passageway 664b connects in fluid communication third passageway 628 and second passageway 626b.

The third passageway 628 is also in fluid connection with conduit 629. Conduit 629 is formed of a flexible plastic and terminates in an adaptor 620 for mating connection with surgical instruments, lavages, cannulas, or other devices for retrieving bodily fluids and tissues. In alternative embodiments, the valve 610 can be fitted with an integral conduit piece (not shown) such as previously described to aid in retrieval of fluid and tissue samples from a patient.

The first passageway 626a is connected through conduit 632a, T-conduit 625, conduit 623 and vacuum adaptor 621 to a standard medical vacuum source (not shown). When the valve is in the first position as shown in FIG. 31, the suction of a vacuum source draws fluid or tissue through a medical instrument (not shown) into conduit 629, through passageways 628, 664a, and 626a of the valve 610, and through conduits 632a, 625, and 623. Tissue or fluids drawn from the patient through this conduit pathway are normally discarded without analysis.

When analysis of fluid or tissue samples is desired, the rotor 650 can be rotated by an operator to break the fluid connection between the third passageway 628 and first passageway 626a, and bring the third passageway 628 into fluid communication with the second passageway 626b. The second passageway 626b is connected in fluid communication with a chamber 673 by a conduit 632b. The chamber 673 is defined by a container wall 672 and holds tissue or fluid samples. The conduit 632b connects to a nipple 678 formed in a cap 676 that is screwed onto a threaded neck 674 of the container 670. Since the chamber 673 of the container 670 is also in fluid connection with the vacuum source by way of conduits 687, 627, 625, and 623, fluid or tissue samples are drawn by suction into the chamber 673 of container 670.

Continued passage of fluid or tissue samples through conduits 687, 627, and 623 is inhibited by, for example, placement of filters that block or obstruct passage of the sample. As illustrated by the broken-away portion of the container 670 in FIG. 31, a filter screen 682 is positioned in the chamber 673. The filter screen 682 is formed to define a plurality of apertures 684 that permit withdrawal of air from chamber 673 through pipe 680 into conduits 687, 627, 623, but prevent passage of tissue samples sized larger than the apertures 684. Additionally, the filter screen 682 can be formed from, or coated with, a hydrophobic material that resists passage of aqueous fluids therethrough. A secondary, in-line filter 690 is also connected between conduits 687 and 627 to reduce passage of samples into conduit 627. The filter 690 includes a filter element 692 connected to conduit 687 and filter element 694 connected to conduit 627. A porous filter pad 696 is positioned in a filter chamber 695 defined between the elements 692 and 694 to trap small bits or tissue or fluid.

In operation, a surgeon or other medical personnel simply rotates the rotor 650 from its first position with tissue passing directly to the vacuum source, to its second position, so that tissue samples are trapped in the container 670. The sample containing container 670 can be disconnected (by unscrewing the cap 676) from the system 600 and taken for laboratory analysis. The remaining, now contaminated, elements of the system 600 are then disposed of by approved medical waste disposal procedures.

Figure 32:
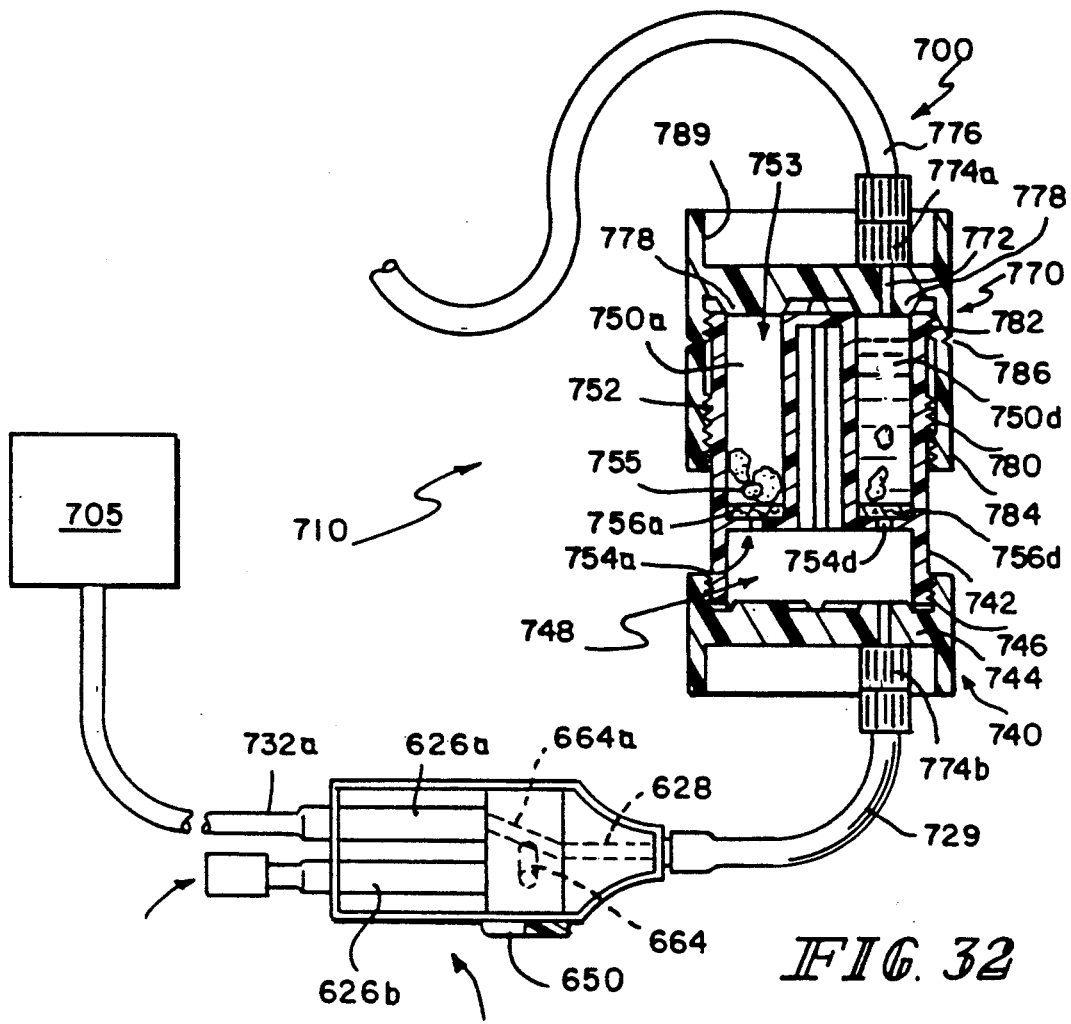
FIG. 32 is a side view of a disposable sample trap having a cap fitted over a sample trap body, the sample trap body defining several chambers into which samples can be drawn by a vacuum and stored.
Figure 33:
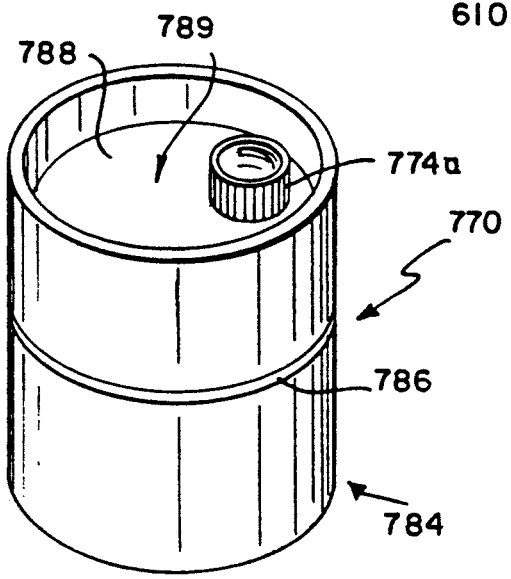
FIG. 33 is a perspective view of the cap.
Figure 34:
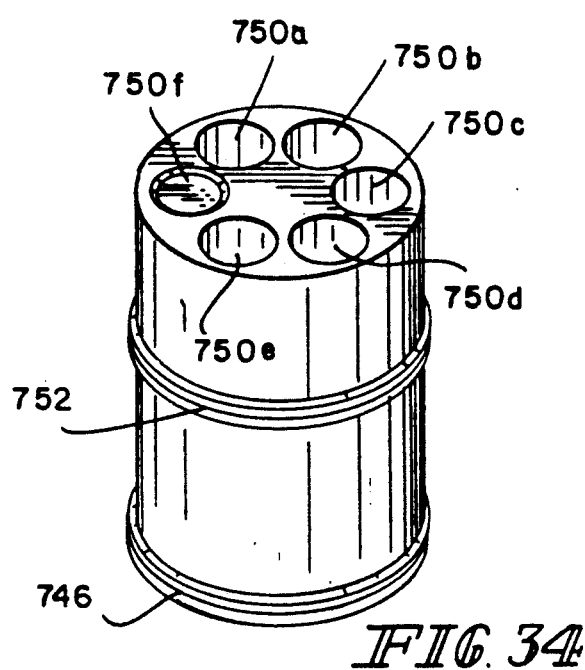
FIG. 34 is a perspective view of a portion of the sample trap body, illustrating five cylindrical chambers and a dummy chamber symmetrically arranged and radially spaced at about the same distance from the center of the sample trap body.

An alternative embodiment of a sample trap system is illustrated in FIGS. 32-34. As best seen in FIG. 32, a sample trap system 700 includes a sample trap 710 that can be connected in fluid communication with a vacuum source 705. This fluid connection is controlled by a dual valve 610 such as described with above with reference to FIG. 31. The first passageway 626a of the dual valve 610 is connected in fluid communication with vacuum source 705 by conduit 732a, and the second passageway 626b is in fluid connection with the atmosphere.

The sample trap system 700 is designed to be a disposable, low-cost apparatus for retaining samples for later laboratory analysis. Accordingly, the exemplified sample trap system 700 is formed from a minimal number of molded, plastic parts. The system 700 includes a sample trap body 740 formed to define chambers 750a, 750b, 750c, 750d, and 750e for holding samples. A dummy chamber 750f that does not hold samples is also defined in the sample trap body 740. A cap 770 fits over the body 740.

The cap 770 is cylindrically configured with a side wall 784 radially dimensioned to fit over the sample trap body 740. A sample conduit 772 is defined through an end wall 788. The end wall 788 is inset within the side wall 784 to form an opening 789. The opening 789 is deep enough to allow positioning a mating adaptor 774a completely within the opening 789. This design allows the trap 700 to flatly rest upon a surface without being unbalanced by a protruding mating adaptor.

The mating adaptor 774a allows fluid connection of the conduit 772 to a conduit 776. The conduit 776 can be connected to a wide variety of medical instruments (not shown) capable of retrieving samples. Fluid or tissue moves from a medical instrument, through the mating adaptor 774 and conduit 772, and into one of the chambers 750. The conduit 772 is selectively positioned at a distance from the center of the cap 770 so that rotation of the cap 770 relative sample trap body 740 will sequentially bring the conduit 772 into fluid communication with each of the chambers 750a-f as the cap 770 is rotated clockwise. The cap 770 is formed to define two separate sets of internal threads 780 and 782, and its sidewall 784 is notched with a circumferential groove 786.

The sample trap body 740 is formed from two permanently attached components 742 and 744. The component 744 is formed by breaking or cutting a cap 770 at its circumferential groove 786 and discarding the piece that does not support a mating adaptor 774b. Internal threads 782 of the component 744 can be coated with an adhesive, and threaded onto external threads 746 of the component 744 for permanent attachment. The components 742 and 744 together define an exit chamber 748 in fluid communication with mating adaptor 774b.

The exit chamber 748 is also in fluid communication with chambers 750a, 750b, 750c, 750d, and 750e defined in the sample trap body 740. These chambers 750a-3, taken in conjunction with the dummy chamber 750f, are symmetrically positioned at about the same distance from the center of the cylindrical trap body 740. This distance substantially corresponds to the distance of the sample conduit 772 from the center of the cap 770. As the cap 770 is rotated clockwise, each chamber 750a-f is respectively brought into fluid communication with the sample conduit 772.

Each chamber 750a-e has an entrance 753 and an exit 754 (e.g. entrance 753a of chamber 750a, exit 754a of chamber 750a), with room to store samples of body fluids or tissue between the entrance and exit. The exits of the chambers 750a-e are in fluid communication with the exit chamber 748 to permit withdrawal of air from the chambers 750a-e. Typically, a filter (e.g. 756a, 756d) is positioned at each of the exits to prevent passage of solids, or solids and fluids, while permitting gas and movement therethrough. Although the embodiment illustrated is provided with individual filters that fit into each chamber 750 a-e, it is also contemplated to provide molded filter elements integrally formed to block passage of tissue. In addition, a single filter pad (not shown) can be situated in the exit chamber 748 to block tissue passage and the individual filters omitted. Other conventional filtration methods known in the art can also be used to block passage of samples from the chambers 750 a-e.

Assembly of the system 700 requires threaded attachment, with optional adhesive, of component 744 to threads 746 defined in component 742 of the sample trap body 740. The cap 770 is then fitted atop the body 740, and threadedly screwed clockwise completely past threads 752 defined in on the body 740. The blocking interaction of threads 752 defined on the body 740 and threads 780 on the cap 770 prevents inadvertent disengagement of the cap 770 from the body 740 even though the threads 752 and 780 are not in screwing engagement with each other. Disengagement of the cap 770 from the body 740 requires pulling the cap 770 upward to engage the threads 752 and 780, and application of a counterclockwise screwing movement to the cap 770 relative to the body 740.

In operation, the combination of body 740 and cap 770, forming a portion of trap 700, is unsealed from sterile packaging (not shown) and connected to a medical instrument (not shown) and a vacuum source 705. The cap 770 is positioned relative to the sample trap body 740 so that the conduit 772 is in fluid communication with the dummy chamber 750f. Connection to the vacuum source is by way of conduit 729, which is connected to the mating adaptor 774b connected to the component 744, and through dual valve 610 and conduit 732a. The dual valve 610 is identical to that described with reference to FIG. 31. The second passageway 626b is in fluid communication with the atmosphere and the first passageway 626a is in fluid communication with the vacuum source 705.

Initially, the conduit 772 defined in the cap 770 is positioned over the dummy chamber 750f. When a predominantly solid tissue sample is to be retrieved for analysis, the cap 770 is rotated clockwise to position the conduit 772 over, for example, chamber 750a. The exit 754a of chamber 750a is blocked with a hydrophilic filter 756a that permits passage of air and aqueous fluids, but prevents passage of solid tissue. The rotary valve 650 is turned so that conduit 729 and exit chamber 748 are brought into fluid communication with the vacuum source 705. The vacuum pulls protuberances 778, integrally defined to extend from the cap 770, tightly against the body 740, acting to seal the chambers 750a-f against inflow of atmospheric air. Additionally, tissue 755 is drawn by the reduced air pressure in chamber 750a through conduit 776 and sample conduit 772 into the chamber 750a. Continued passage of the tissue 755 into the exit chamber 748 is prevented by the hydrophilic filter 756a. When the chamber 750a is filled, or a large enough sample has been taken, the cap 770 is rotated clockwise to bring the conduit 772 over the next chamber 750b. This process can be repeated until the sampling procedure is finished.

When samples containing liquid are desired for analysis, the cap 770 is rotated clockwise to position the conduit 772 over, for example, the chamber 750d. The exit 754d of chamber 750d is blocked with a hydrophobic filter 756d that permits passage of air, but prevents passage of both solid tissue and aqueous fluids. The rotary valve 650 is turned so that conduit 729 and exit chamber 748 are brought into fluid communication with the vacuum source 705. The vacuum pulls the cap 770 tightly against the body 740, and additionally pulls tissue 755 and fluid 757 through conduit 776 and sample conduit 772 into the chamber 750d.

Disconnection of the cap 770 from the body 740 generally requires turning the rotary valve 650 of the dual valve 610 until the second passageway 626b is brought into fluid communication with third passageway 628. Air rushes into the body 740, breaking the vacuum seal between the protuberances 778 on the cap 770 and the body 740. The operator of the system 700 can then pull upward on the cap 770 to engage the threads 780 and 752, and the cap 770 is unscrewed counterclockwise. The body 740 can be disconnected from the conduit 729, and optionally sealed with a secondary cap or plugs (not shown) and transferred for laboratory analysis. Alternatively, the cap 770 can simply be rotated to bring the conduit 772 over the dummy chamber 750f, and the complete unit 770 transferred for laboratory analysis. The components of the system 700 are disposed of as medical waste after the samples have been removed.

Figure 35:
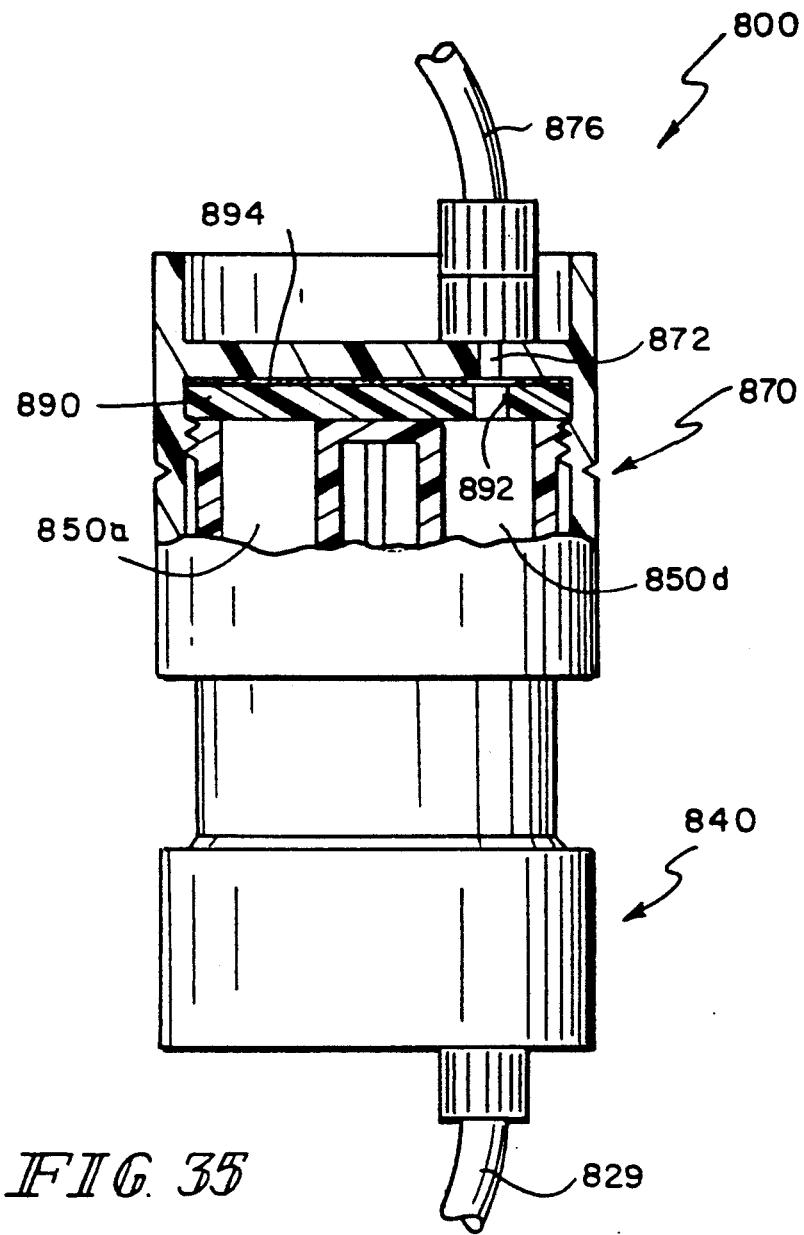
FIG. 35 is a view of a disposable sample trap, partially cut away to illustrate a resilient seal positioned between the trap's cap and body.

FIG. 35 illustrates a trap 800 having a structure and operation substantially the same as the embodiment described in FIGS. 32–34. However, the mechanism for sealing the chambers defined in the body 840 is slightly different from the foregoing embodiments of the invention. Instead of sealing chambers with protuberances defined in the cap, a resilient pad 890 is positioned between a cap 870 and the body 840 to seal chambers (chambers 850a and 850d are illustrated in cross section) defined in the body 840. The resilient pad 890 is formed to define an aperture 892 therethrough, and the pad 890 is permanently attached with an adhesive 894 to the cap 870 so that the aperture 892 is in fluid communication with conduits 872 and 876. The resilient pad 890 is generally disc shaped, and dimensioned to be slightly compressed when the cap 870 is fitted over the body 840, thereby sealing the chambers. When air pressure in the chambers is reduced, the cap 870 is tightly pulled against the body 840, compressing the resilient seal 890 even more, and acting to provide a substantially airtight seal.

Figures 36, 37:
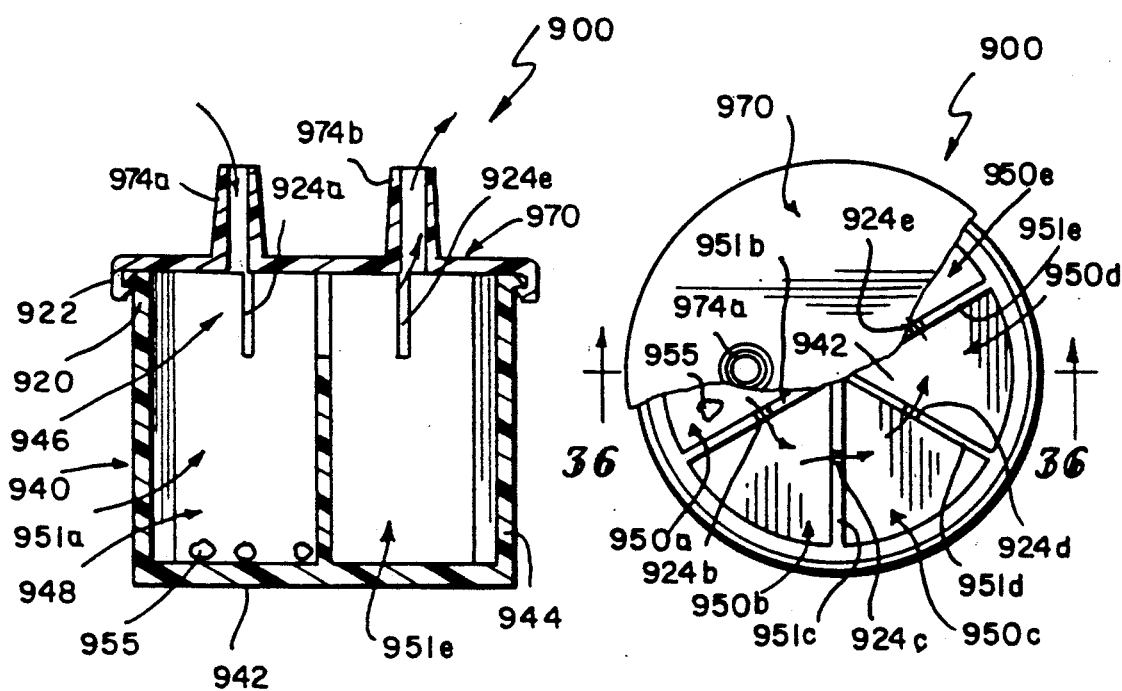
FIG. 36 is a view taken along line 36—36 of FIG. 37 of a two-piece disposable sample trap having a sample conduit and a vacuum port defined in a cap.
FIG. 37 is a top view of the two-piece disposable sample trap, with the cap partially broken away to show a plurality of chambers into which samples can be drawn and stored until analysis.

Another embodiment of the invention is illustrated in FIGS. 36–37, which show a sample trap system 900. The sample trap system 900 is inexpensively constructed from two integral molded parts, a sample trap body 940 and a cap 970.

The sample trap body 940 has a generally cylindrical configuration, with an integrally formed bottom wall 942 and side wall 944. The bottom wall 942 lies adjacent to a lower end 948, and distant from an open upper end 946. The side wall 944 is formed to have a rim 920 at its open upper end 946, with the rim 920 capable of engaging and holding a lip 922 defined in the cap 970. The interior of the sample trap body 940 is configured to form multiple dividers 951a, 951b, 951c, 951d, and 951e defining a plurality of chambers, of which chambers 950a, 950b, 950c, 950d, and 950e are shown in FIG. 37. All of the chambers are in gas communication with each other because of the provision of slots in the chamber dividers (slots 924a and 924e shown in FIG. 36, slots 924b, 924c, 924d, and 924e shown in FIG. 37).

The cap 970 is formed to define a sample conduit 974a for admitting samples 955 into the chambers 950a-e of the sample trap body 940. A vacuum port 974b for connection to a vacuum source (not shown) is also defined in the cap 970. The cap 970 is generally disc-shaped, and dimensioned to conformably fit over the sample trap body 940. Engagement requires initially flexing the lip 922 outward over the rim 920 while pressing the cap 970 toward the sample trap body 940 until the lip 922 can inwardly spring to engage and hold the rim 920. Although this attaches the cap 970 to the sample trap body 940, the cap 970 is still rotatably movable with respect to the sample trap body 940. Rotation of the cap 970 relative to the sample trap body 940 allows a user to position the sample conduit 974a over any of the chambers.

Of course, other conventional attachment mechanisms including screwing attachment, lugs fittable into notches, friction tight tapered inserts, or other known attachment methods can be used to fix the cap 970 to the sample trap body 940.

Reducing air pressure in the chambers of the sample trap body 940 acts to draw samples 955 from the sample conduit 974a (which in turn is connected through a conduit to a medical suctioning device, not shown) into each one of the chambers as the cap is rotatably moved to position the sample conduit over each chamber. A vacuum is drawn by connecting the chambers, all of which are in gas communication with each other, to a vacuum source (not shown). Samples 955 drawn into one of the chambers, for example chamber 950a, and are prevented from moving into the other chambers by the small size of the slots and by the tendency of the sample to gravitationally settle against the bottom wall 942.

A dual valve 610 (not shown in FIGS. 36–37) such as previously disclosed and illustrated in FIG. 31, can be connected between the vacuum source and the vacuum port 974b to control application of the vacuum and consequent sample retrieval. Other conventional mechanism for controlling application of a vacuum to the chamber are contemplated.

What is claimed is:

1. A disposable sample trap system, the system comprising:
   a cylindrical hollow sample trap body formed with a bottom end wall and an upper open end and with multiple dividers extending across the hollow of the body to divide the hollow of the body into a plurality of chambers;

a cap rotatably attached to and sealing said open end of the trap body;

inlet conduit means attached to an opening in the cap to allow for passage of fluid and samples through the cap opening into one of the plurality of chambers which is aligned with the opening;

outlet conduit means connected to one of the plurality of cambers and connectible to a vacuum source;

narrow slots in the dividers to fluidly connect the inlet conduit means to the outlet conduit through the plurality of chambers; and wherein the cross-sectional area of the narrow slots is less than a cross-sectional area of the opening and samples so that when the outlet conduit means is connected to a vacuum source, the vacuum causes fluid and samples to be drawn into the one of the plurality of chambers through the inlet passage while allowing the fluid entering into the one of the plurality of chambers to pass through at least one of the slots to the outlet and trapping the sample in the one of the plurality of chambers, since the sample cannot pass through the slot.

2. The sample trap system of claim 1, wherein the outlet conduit is connected in fluid communication with a third passageway of a vale, the valve providing first and second passageways alternately in fluid communication with the third passageway, and the first passageway being connected to a vacuum source and the second passageway being in fluid connection with the atmosphere.

3. The disposable trap of claim 1 wherein the outlet conduit is located in the rotatable cap.

4. The disposable trap of claim 1 wherein the rotatable cap is attached to the trap body through an attaching means including a rim defined by the trap body and a lip defined by the cap and configured to engage the rim.

* * * * *